Figure 1A:
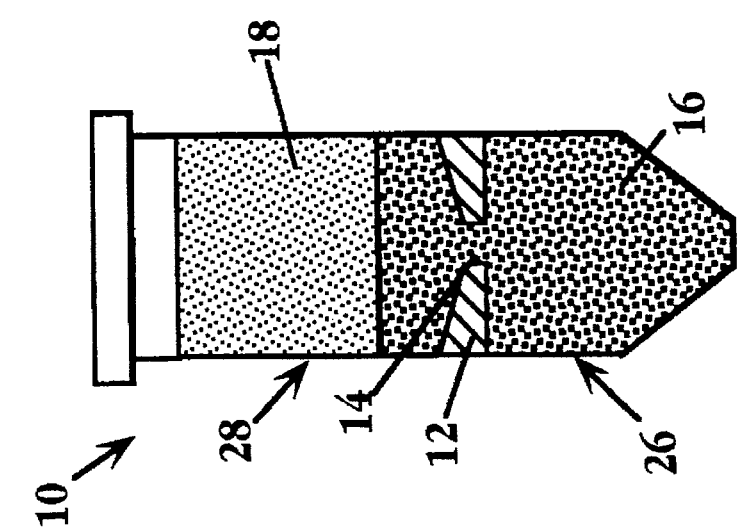

United States Patent [19]
Van Vlasselaer

[11] Patent Number: 5,646,004
[45] Date of Patent: *Jul. 8, 1997

[54] METHODS FOR ENRICHING FETAL CELLS FROM MATERNAL BODY FLUIDS

[75] Inventor: Peter Van Vlasselaer, Sunnyvale, Calif.

[73] Assignee: Activated Cell Therapy, Inc., Mountain View, Calif.

[*] Notice: The term of this patent shall not extend beyond the expiration date of Pat. No. 5,474,687.

[21] Appl. No.: 299,468

[22] Filed: Aug. 31, 1994

[51] Int. Cl.⁶ .......................... G01N 33/555; B01L 11/00
[52] U.S. Cl. .......................... 435/7.25; 210/781; 210/782; 435/2; 435/7.21; 435/7.24; 435/803; 436/514; 436/518; 436/527; 436/824; 422/72; 422/101; 422/102
[58] Field of Search .......................... 210/781, 782; 436/514, 518, 527, 824; 422/72, 101, 102; 435/2, 7, 21, 7.24, 7.25, 803

[56] References Cited

U.S. PATENT DOCUMENTS

| | | |
|---|---|---|
| 3,441,205 | 4/1969 | Young, Jr. . |
| 3,513,976 | 5/1970 | James . |
| 3,706,305 | 12/1972 | Berger et al. ............... 128/762 |
| 3,706,306 | 12/1972 | Berger et al. ............... 128/762 |
| 3,750,645 | 8/1973 | Bennett et al. .............. 128/760 |
| 3,849,072 | 11/1974 | Ayres ............................ 210/789 |
| 3,862,303 | 1/1975 | Anderson ..................... 436/531 |
| 3,937,211 | 2/1976 | Merten ......................... 128/765 |
| 3,957,654 | 5/1976 | Ayres ............................ 210/516 |
| 3,957,741 | 5/1976 | Rembaum et al. .......... 526/312 |
| 3,965,889 | 6/1976 | Sachs ............................ 128/764 |
| 3,985,122 | 10/1976 | Topham ....................... 128/765 |
| 4,001,122 | 1/1977 | Griffin ......................... 210/516 |
| 4,020,831 | 5/1977 | Adler ........................... 128/765 |
| 4,022,576 | 5/1977 | Parker ......................... 436/177 |
| 4,035,316 | 7/1977 | Yen et al. .................... 521/65 |
| 4,040,959 | 8/1977 | Berman et al. .............. 210/782 |
| 4,055,501 | 10/1977 | Cornell ........................ 210/516 |
| 4,066,414 | 1/1978 | Selby ............................ 422/102 |
| 4,105,598 | 8/1978 | Yen et al. .................... 521/53 |
| 4,112,924 | 9/1978 | Ferrara et al. ............... 128/764 |
| 4,134,512 | 1/1979 | Nugent ......................... 215/247 |

(List continued on next page.)

FOREIGN PATENT DOCUMENTS

| | | |
|---|---|---|
| 198462A3 | 10/1986 | European Pat. Off. . |
| 2115032 | 3/1971 | Germany . |
| WO91/07660 | 5/1991 | WIPO . |
| WO93/08268 | 4/1993 | WIPO . |
| WO93/08269 | 4/1993 | WIPO . |

OTHER PUBLICATIONS

Bianchi et al., "Isolation of fetal DNA from nucleated erythrocytes in maternal blood," *Proc. Nat. Acad. Sci.*, vol. 87, pp. 3279–3283 (1990).

Wallach et al., "Affinity Density Perturbation: A New Fractionation Principle and Its Illustration in a Membrane Separation," *FEBS Letters*, vol. 21, No. 1, pp. 29–33, (1972).

"The CD System," Dako, Inc. (1990).

(List continued on next page.)

Primary Examiner—Lora M. Green
Assistant Examiner—Susan C. Wolski
Attorney, Agent, or Firm—Carol A. Stratford; Debra J. Glaister; Peter J. Dehlinger

[57] ABSTRACT

The present invention relates to methods of enriching fetal cells from maternal body fluids. In particular, it relates to the use of a cell-trap centrifugation tube containing a gradient solution adjusted to a specific density to enrich for fetal nucleated red blood cells from maternal blood. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to undesired cell populations allowing the fetal cells to be separated during centrifugation in a more convenient manner. The rapid fetal cell enrichment method described herein has a wide range of applications, including but not limited to, gender determination and prenatal diagnosis of genetic diseases without the use of invasive procedures.

19 Claims, 6 Drawing Sheets

U.S. PATENT DOCUMENTS

| | | | |
|---|---|---|---|
| 4,147,628 | 4/1979 | Bennett et al. | 210/789 |
| 4,152,270 | 5/1979 | Cornell | 210/516 |
| 4,181,700 | 1/1980 | Chervenka et al. | 422/102 |
| 4,203,840 | 5/1980 | Stoeppler | 210/787 |
| 4,213,456 | 7/1980 | Böttger | 604/226 |
| 4,256,120 | 3/1981 | Finley | 128/764 |
| 4,378,812 | 4/1983 | Sarstedt | 128/765 |
| 4,443,345 | 4/1984 | Wells | 210/782 |
| 4,459,997 | 7/1984 | Sarstedt | 128/764 |
| 4,510,244 | 4/1985 | Parks et al. | 435/172.2 |
| 4,511,349 | 4/1985 | Nielsen et al. | 494/16 |
| 4,511,662 | 4/1985 | Baran et al. | 436/513 |
| 4,533,468 | 8/1985 | Ensor et al. | 209/172 |
| 4,562,844 | 1/1986 | Carpenter et al. | 128/765 |
| 4,569,764 | 2/1986 | Satchell | 210/511 |
| 4,610,846 | 9/1986 | Martin | 422/101 |
| 4,707,276 | 11/1987 | Dodge et al. | 210/789 |
| 4,710,472 | 12/1987 | Saur et al. | 435/308.1 |
| 4,777,145 | 10/1988 | Luotola et al. | 436/526 |
| 4,824,560 | 4/1989 | Alspector | 209/208 |
| 4,828,716 | 5/1989 | McEwen et al. | 210/740 |
| 4,844,818 | 7/1989 | Smith | 210/789 |
| 4,886,071 | 12/1989 | Mehl et al. | 128/760 |
| 4,917,801 | 4/1990 | Luderer et al. | 210/516 |
| 4,927,749 | 5/1990 | Dorn | 435/2 |
| 4,927,750 | 5/1990 | Dorn | 435/2 |
| 4,954,264 | 9/1990 | Smith | 210/782 |
| 4,957,638 | 9/1990 | Smith | 210/782 |
| 4,983,369 | 1/1991 | Barder et al. | 423/338 |
| 5,030,341 | 7/1991 | McEwen et al. | 210/94 |
| 5,030,559 | 7/1991 | Nicolson et al. | 435/7.23 |
| 5,039,401 | 8/1991 | Columbus et al. | 210/177 |
| 5,045,201 | 9/1991 | Dubois et al. | 210/502.1 |
| 5,053,134 | 10/1991 | Luderer et al. | 210/516 |
| 5,132,232 | 7/1992 | Parker | 436/177 |
| 5,236,604 | 8/1993 | Fiehler | 210/782 |
| 5,248,480 | 9/1993 | Greenfield et al. | 422/68.1 |
| 5,260,186 | 11/1993 | Cercek et al. | 435/2 |
| 5,269,927 | 12/1993 | Fiehler | 210/516 |
| 5,271,852 | 12/1993 | Luoma, II | 210/789 |
| 5,279,936 | 1/1994 | Vorpahl | 435/6 |
| 5,308,506 | 5/1994 | McEwen | 210/745 |
| 5,314,074 | 5/1994 | Inbar | 209/208 |
| 5,474,687 | 12/1995 | Van Vlasselaer | 210/782 |

OTHER PUBLICATIONS

Herzenberg et al., 1979, "Fetal Cells in the Blood of Pregnant Women: Detection and Enrichment by Fluorescence–Activated Cell Sorting" *Proc. Natl. Aca. Sci, USA* 76: 1453–5.

Price et al., 1991, "Prenatal diagnosis with fetal cells isolated from maternal blood by multiparameter flow cytometry," *Am. J. Obstet. Gynecol.* 165(6), part 1):1731–1737.

Elias et al., 1992, Session 12: Plenary Session, "Prenatal diagnosis of aneuploidy using fetal cells isolated from maternal blood" *Am. J. Hum. Genet*, 51:A4, Excerpt 5.

Ganshirt–Ahlert et al., 1992, Session 34: Prenatal and Perinatal Genetics II, and Molecular Applications in Clinical Genetics III, "Noninvasive prenatal diagnosis," *Am. J. Hum. Genet.* 51:A48 Excerpt 182.

Harrison et al., 1992, Prenatal and Perinatal Genetics, "Use of fluorescence in situ hybridization to detect confined placental mosaicism in trisomic conceptions," *Am. J. Hum. Genet.* 51:A257, Excerpt 1014.

Holzgreve et al., 1992, "Fetal Cells in the Maternal Circulation," *J. Reprod. Med.* 37(5):410–418.

Julien et al., 1992, Session 34: Prenatal and Perinatal Genetics II, and Molecular Applications in Clinical Genetics III, "Fetal cells in maternal blood," *Am. J. Hum. Genet.* 51:A48, Excerpt 181.

Russo et al., 1992, *The Use of Resealed Erythrocytes as Carrier's and Bioreactors*, Published by Magnani & DeLoach, Plenun Press, New York, pp. 101–107.

Dicke et al., 1968, "The Selective Elimination of Immunologically Competent Cells From Bone Marrow and Lymphatic Cell Mixtures," *Transplantation* 6(4):562–570.

Dicke et al., 1970, "Avoidance of Acute Secondary Disease by Purification of Hemopoietic Stem Cells with Density Gradient Centrifugation," *Exp. Hematol.* 20:126–130.

Dicke et al., 1971, "Allogeneic Bone Marrow Transplantation After Elimination of Immunocompetent Cells by Means of Density Gradient Centrifugation," *Transplantation Proceedings* 3(1):666–668.

Dicke et al., 1973, "The Use of Stem Cell Concentrates As Bone Marrow Grafts in Man," *Transplantation Proceedings* 5(1):909–912.

Korbling et al., 1977, "Procurement of Human Blood Stem Cells by Continuous–Flow Centrifugation —Further Comment," *Blood* 50:753–754.

Korbling et al., 1977, "In–Vitro and In–Vivo Properties of Canine Blood Mononuclear Leukocytes Separated by Discontinuous Albumin Density Gradient Centrifugation," *Biomedicine*, 26:275–283.

Olofsson et al., 1980, "Separation of Human Bone Marrow Cells in Density Gradients of Polyvinylpyrrolio Coated Silica Gel (Percoll)," *Scand. J. Hemattol.* 24:254–262.

Osborne et al., 1980, "The Value of Estrogen and Progesterone Receptorsin the Treament of Breast Cancer" *Cancer* 46(12):2884–8.

Westley et al., 1980, "An Estrogen–Induced Protein Secreted By Human–Breast Cancer Cells in Culture" *European Journal of Cell Biology* 22(1):397.

Gerdes et al., 1983 "Production of a Mouse Monoclonal Antibody Reactive with a Human Nuclear" *Current Biotech Abs*.

Ellis et al., 1984, "The Use of Discontinuous Percoll Gradients to Separate Populations of Cells from Human Bone Marrow and Peripheral Blood," *J. of Immunological Methods* 66:9–16.

Kufe et al., 1984, "Differential Reactivity of a Novel Monoclonal Antibody (DF3) with Human Malignant Versus Benign Breast Tumors" *Hybridoma* 3(3):223–32.

Lasky et al., 1985, "Size and Density Characterization of Human Committed and Multipotent Hematopoietic Progenitors" *Exp. Hematol.* 13:680–4.

Martin et al., 1986, "Purification of Haemopoietic Progenitor Cells From Patients with Chronic Granulocytic Leukaemia Using Percoll Density Gradients and Elutriation" *Brit. J. Haematol.* 63:187–98.

Bray et al., 1987 "Serum Levels and Biochemical Characteristics of Cancer–Associated Antigen CA–549, a Circulating Breast Cancer Marker" *Cancer Res* 47(22):5853–60.

Shpall et al., 1991, "Immunomagnetic purging of breast cancer from bone marrow for autologous transplantation," *Bone Marrow Transplantation* 7:145–151.

Yoshioka et al., 1991, "Immobilization of ultra–thin layer of monoclonal antibody on glass surface," *J. of Chromolography* 566:361–368.

Durrant et al., 1992 "A Rapid Method for Separating Tumour Infiltrating Cells and Tumour Cells from Colorectal Tumours" *J. Immunol. Meth.* 147:57–64.

Ganshirt-Ahlert et al., 1992, "Magnetic cell sorting and the transferrin receptor as potential means of prenatal diagnosis from maternal blood," *Am. J. Obstet. Gynecol,* 166(5):1350–1355.

Hall et al., 1992 Prenatal and Perinatal Genetics, "Isolation Purification of CD34+ Fetal Cells From Maternal Blood," *Am. J. Hum. Genet.* 51:A257, Excerpt 1013.

Ikuta et al., 1992, "Lymphocyte Development From Sterm Cells", *Ann. Rev. Immunol.* 10:759–83.

Lebkowski et al., 1992, "Rapid Isolation of Human CD34 Hematopoietic Stem Cells Purging of Human Tumor Cells", *Transplantation* 53(5):1011–1019.

Pope et al., 1993, "New Application of Silane Coupling Agents for Covalently Binding Antibodies to Glass and Cellulose Solid Supports," *Bioconjugate Chem.* 4:166–171.

Schmitz et al., 1993, "Optimizing follicular dendritic cell isolation by discontinuous gradient centrifugation and use of the magnetic cell sorter (MACS)," *J. of Immunological Methods* 139:189–196.

Simpson et al., 1993, "Isolating Fetal Cells From Maternal Blood, Advances in Prenatal Diagnosis Through Molecular Technology," *Journal of American Medical Association (JAMA)* 270(19):2357–2361.

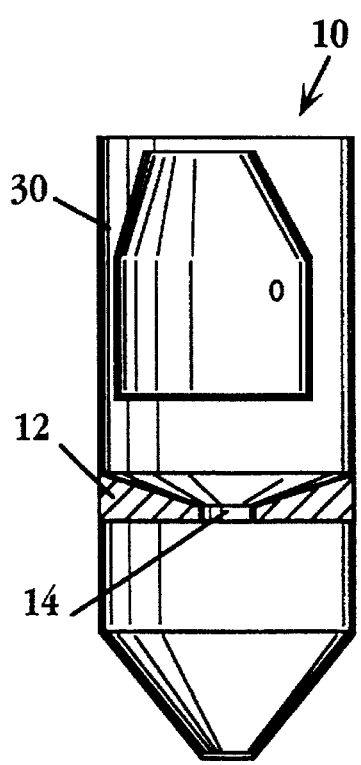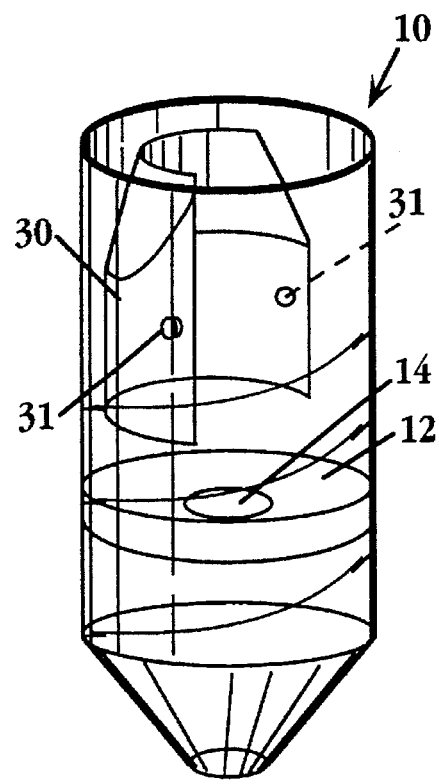
Fig. 2A                Fig. 2B
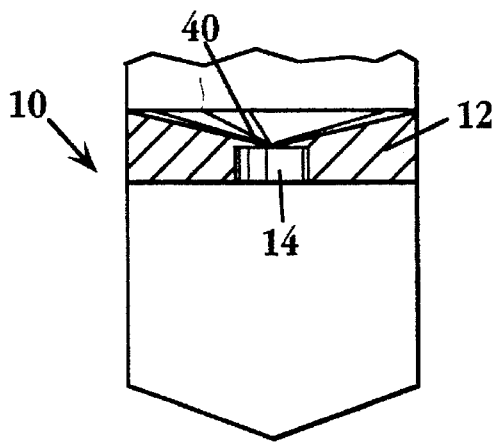
Fig. 3

METHODS FOR ENRICHING FETAL CELLS FROM MATERNAL BODY FLUIDS

1. INTRODUCTION

The present invention relates to methods of enriching fetal cells from maternal body fluids. In particular, it relates to the use of a cell-trap centrifugation tube containing a gradient solution adjusted to a specific density to enrich for fetal nucleated red blood cells from maternal blood. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to undesired cell populations allowing the fetal cells to be separated during centrifugation in a more convenient manner. The rapid fetal cell enrichment method described herein has a wide range of applications, including but not limited to, gender determination and prenatal diagnosis of genetic diseases without the use of invasive procedures.

2. BACKGROUND OF THE INVENTION

A variety of human diseases are caused by genetic aberrations. Such aberrations may be due to gene mutations or chromosomal abnormalities. The application of recombinant DNA technology to the study of genetic diseases has greatly increased the knowledge regarding their molecular basis. As a result, the accuracy of diagnosis of a number of genetic diseases has substantially improved in recent years.

In addition, prenatal diagnosis of certain chromosomal abnormalities has become a routine procedure in clinical medicine. Such diagnosis is usually performed in cases where the parental age is relatively advanced, or there is a family history of inherited diseases. For instance, it has been recommended that pregnant women over the age of 35 undergo prenatal diagnosis. At present, the diagnosis is carried out by a procedure known as amniocentesis which involves the aspiration of a small sample of amniotic fluid from the pregnant mother, culturing the fetal cells in the fluid, and determining the karyotype of the fetal cells. More recently, chorionic villus sampling has also been used, which involves the direct transcervical and transabdominal aspiration of the chorionic villus. However, since both amniocentesis and chorionic villus sampling require invasive procedures for obtaining fetal cells, they inevitably expose both the mother and the fetus to a certain amount of risk. Therefore, non-invasive approaches to prenatal diagnosis are preferred.

It has now been established that a small number of fetal cells circulate in maternal blood, which provide an alternative and desirable source of materials for prenatal genetic testing (Simpson and Elias, 1993, JAMA 270:2357). However, in order to successfully utilize maternal blood for prenatal diagnosis, it is recognized that the small number of fetal cells must first be enriched, and one must employ highly sensitive and specific techniques to detect the fetal cells (Holzgreve et al., 1992, J. Reprod. Med. 37:410). While several detection methods have been made available through recent advances, including polymerase chain reaction (PCR) and fluorescence in situ hydribization (FISH), the major difficulty in the routine use of maternal blood for prenatal diagnosis is the inability to enrich the small number of fetal cells in a mixture of maternal cells to yield reliable diagnostic results.

One of the ideal fetal cell populations in maternal blood is nucleated red blood cells. Although there have been wide variations in the estimation of the ratio of fetal nucleated red blood cells to maternal red blood cells, one recent report estimates approximately one fetal cell to $1\times10^7$–$1\times10^8$ maternal cells (Simpson and Elias, 1993, JAMA 270:2357). Thus, due to the extreme rarity of fetal cells in maternal blood, a number of cell separation schemes have been designed to enrich fetal cells prior to genetic testing, including the use of fluorescence-activated cell sorting (Herzenberg et al., 1979, Proc. Natl. Aca. Sci. USA 76:1453), magnetic-activated cell sorting (Ganshirt-Ahlert et al., 1992, Am. J. Obstet. Gynecol. 166:1350) or a combination of these procedures (Ganshirt-Ahlert et al., 1992, Am. J. Hum. Genet. 51:A48). While these procedures have been able to partially enrich fetal cells, they are both costly because of the need for sophisticated instrumentation, and cumbersome due to multiple steps. More importantly, the currently used enrichment methods all result in substantial cell loss, thereby reducing the number of fetal cells for subsequent analysis. Thus, the low number of fetal cells in maternal blood has precluded their use in routine prenatal testing. At present, there remains a need for a rapid and reproducible procedure suitable for processing a large volume of whole blood, and which produces high-yield enrichment of fetal cells from maternal blood.

3. SUMMARY OF THE INVENTION

The present invention relates to methods of enriching fetal cells from maternal body fluids such as peripheral blood, and cell-trap centrifugation tubes with a constriction for use in rapid and high yield isolation of such cells. Recent reports have shown that a small number of fetal cells circulate in the maternal blood. The ability to isolate such fetal cells from the peripheral blood for use in prenatal genetic testing would circumvent conventional methods which involve invasive procedures such as amniocentesis. However, current methods for isolating fetal cells from the blood require multiple steps which result in cell loss, thereby substantially decreasing the total number of fetal cells available for subsequent analysis.

The invention is based, in part, on Applicant's discovery that colloidal silica (PERCOLL) solution adjusted to a density of 1.0720±0.0005 gr/ml, an osmolality of 280 mOsm/kg $H_2O$, and pH 7.4 efficiently separates fetal cells from the majority of adult blood cells when complete blood without prior separation or dilution is overlaid on the gradient solution. In addition, the method is improved by using cell-trap centrifugation tubes described herein which contain a constriction to allow the cells in the upper portion (i.e., above the constriction) to be decanted as opposed to using a pipette to collect the cells which results in increased cell loss. The efficiency of the method is further improved when it is combined with the use of antibodies conjugated to heavy carrier particles in a manner by which the antibodies bind to antigens expressed by undesired cell populations, causing them to have a higher density so that they are pelleted during centrifugation. This method is hereinafter referred to as density adjusted cell sorting. Thus, this specific embodiment of the invention provides for a rapid and high yield procedure to enrich for fetal cells from a large blood volume. The increased number of fetal cells in the resultant cell population enhances the sensitivity and accuracy of techniques commonly applied to genetic testing.

In brief, the present invention may be practiced by overlaying whole blood on a defined density gradient in a cell-trap centrifugation tube, and after centrifugation the cells in the interface collected and pelleted by another centrifugation step to remove cell debris, platelets, and the remainder of the density material. Thereafter, the cells are depleted of the majority of leukocytes by their reactivity with an antibody; the remaining red blood cells analyzed by flow cytometry, and the fetal cells within this population identified by FISH using specific molecular probes. Alternatively, the density adjusted cell sorting procedure further improves the efficiency of this procedure by combining density gradient centrifugation with the antibody depletion steps into a single step, and the interface cells are collected and pelleted to remove cell debris and platelets. In an effort to further minimize cell loss, but achieve platelet removal, the second centrifugation step for pelleting the fetal nucleated red blood cells may also be carried out in a cell-trap tube.

A wide variety of uses is encompassed by the invention described herein, including but not limited to, the rapid and high yield isolation of fetal cells for gender determination and detection of genetic disorders involving gene mutations and chromosomal abnormalities, using techniques such as PCR and FISH.

4. BRIEF DESCRIPTION OF THE DRAWINGS

Figure 1B:
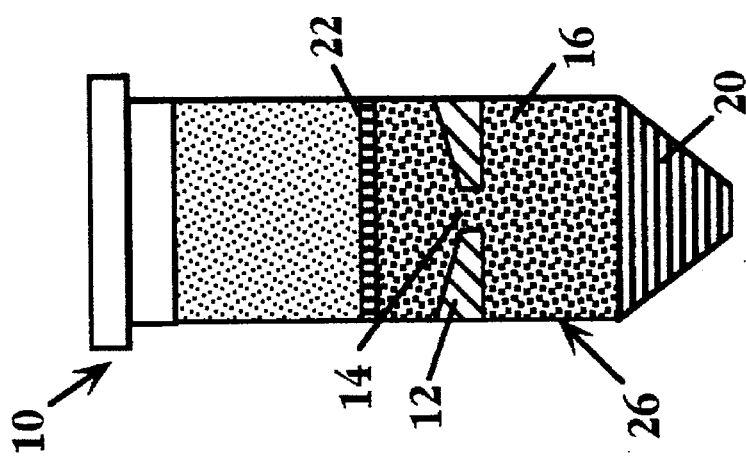
Figure 1C:
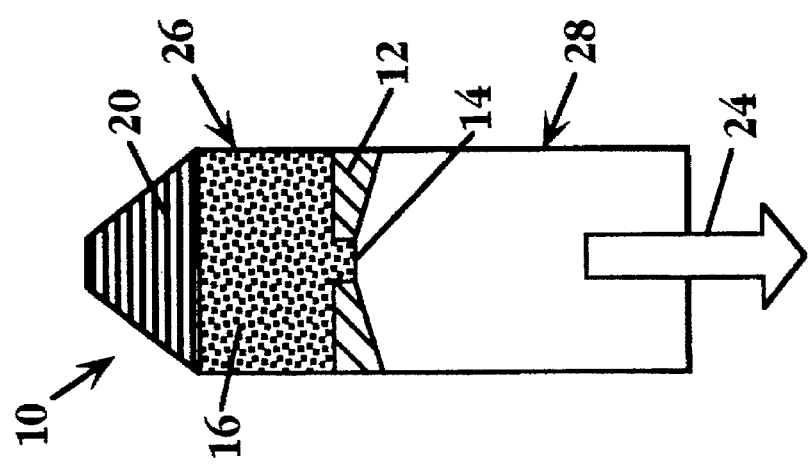

FIGS. 1A–C Cross-sectional views of a preferred embodiment of the centrifugation tube according to the present invention, illustrating the steps of isolating or separating cells according to the invention.

FIG. 2A A schematic cross-sectional view of an alternative preferred embodiment of the present invention.

FIG. 2B A perspective view of the embodiment of FIG. 2A.

FIG. 3 A cross-sectional view of an alternative embodiment of the constriction member of the invention with a valve.

FIGS. 4A–E Examples of alterative shapes of the opening in the constriction member.

FIGS. 5A–F Cross-sectional views of alternative embodiments of the tube and constriction member of the invention.

Figures 6A, 6B:
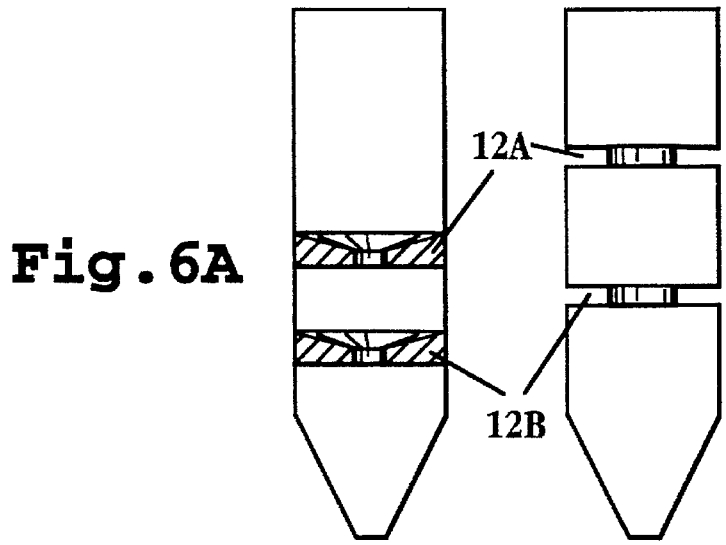

FIGS. 6A and 6B Cross-sectional views of further alternative embodiments of the invention having multiple constriction members.

FIG. 7A–7D A schematic drawing demonstrating the density adjusted cell sorting procedure.

Figure 8A:
Figure 8B:
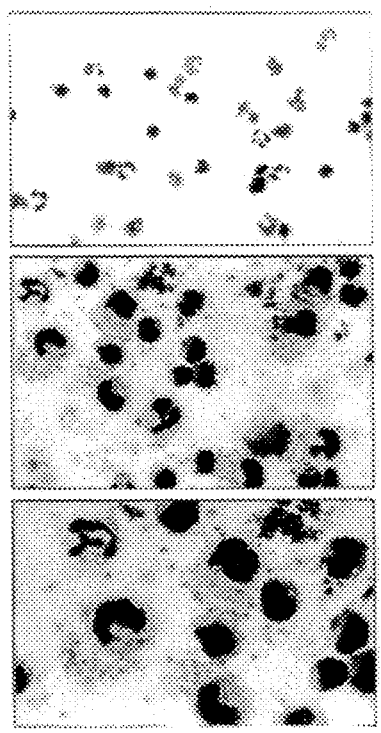
Figure 8C:
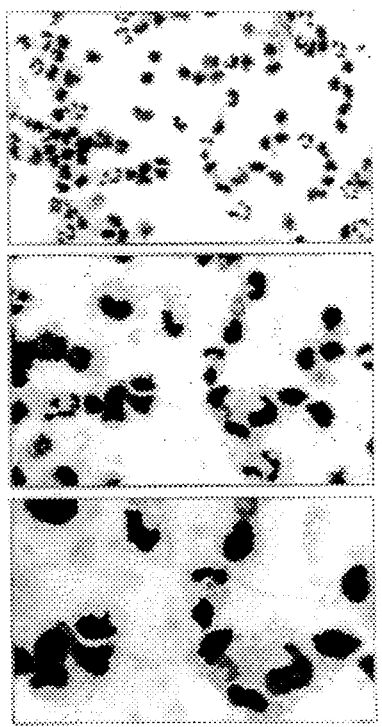

FIG. 8A–8C A comparison of cell numbers in three cell preparations isolated by the conventional method using "FICOLL" as the density material (FIG. 8A, "FICOLL" plus cell-trap tubes (FIG. 8B), and adjusted "PERCOLL" density gradient plus cell-trap tubes (FIG. 8C).

Figure 9A:
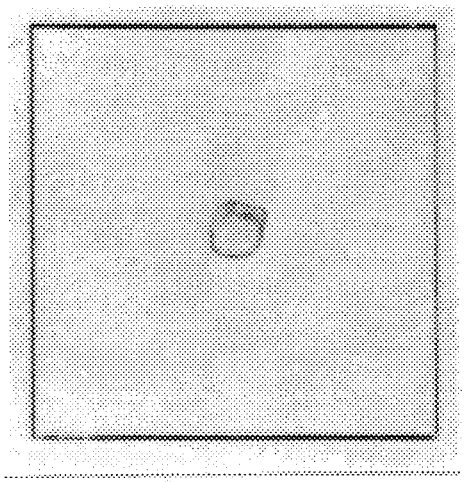
Figure 9B:
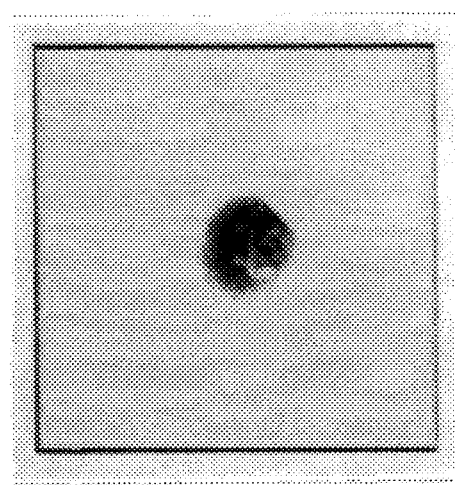
Figure 9C:
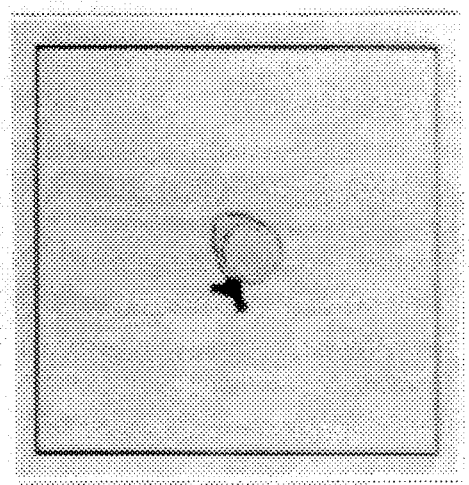

FIG. 9A–9C An identification of nucleated red blood cells isolated by "PERCOLL" centrifugation in cell-trap tubes followed by anti-CD45 depletion.

5. DETAILED DESCRIPTION OF THE INVENTION

5.1. FETAL CELL TYPES IN PREGNANT FEMALES

Fetal cells have been detected in maternal circulation during certain stages of gestation (Holzgreve et al., 1992, *J. Reprod. Med.* 37:410; Simpson et al., 1993, *JAMA* 270:2357). In particular, the three fetal cell types in maternal blood that are accessible to prenatal diagnosis are lymphocytes, trophoblasts and nucleated red blood cells. The present invention encompasses methods of enriching all three cell types from maternal body fluids for use in prenatal genetic testing. However, although all three fetal cell types may be used towards this goal, they possess different advantages due to their inherent properties.

For example, while isolated fetal lymphocytes can be cultivated with relative ease for use as fetal metaphases, the long half life of lymphocytes may yield ambiguous results. It is not uncommon for lymphocytes to persist in the pregnant mother for several years, so that isolation of such cells may produce results that relate to earlier pregnancies. Thus, although fetal lymphocytes are useful for prenatal testing during first pregnancies, their value in prenatal diagnosis declines thereafter due to their long half life in potentially obscuring results for later pregnancies. However, it should be noted that lymphocytes are useful in the appropriate settings because of the large number of available immunologic reagents against their cell surface molecules, and the large body of knowledge regarding their growth in culture.

Fetal trophoblasts are also candidates for use in prenatal diagnosis because of their intimate relationship with the uterus. These cells have a tendency to form syncytia which are multinucleated cells, and as such, they are not suitable for techniques such as FISH because the many nuclei within a cell would potentially obscure the detection of fluorescence staining pattern under the microscope. On the other hand, because of the multi-nucleation, trophoblasts may be particularly suited for providing genetic material for PCR analysis.

At present, the ideal fetal cell type for prenatal diagnosis is nucleated red blood cells. Nucleated red blood cells are extremely rare in the adult peripheral blood. The nuclei of these cells provide a source of genetic material for the application of techniques such as PCR and FISH. There are also several well-known commercially available antibodies that may be used for their characterization, such as anti-CD71 and anti-glycophorin A. Another major advantage for targeting fetal cells in the erythroid lineage is their relatively short life span. Unlike lymphocytes, these cells should not persist from prior pregnancies to interfere with the analysis of maternal blood.

Fetal red blood cells have been found in maternal circulation up to week 20 of pregnancy, but their number rapidly decreases thereafter. Thus, the optimal time period for obtaining maternal blood for the isolation of fetal cells is between week 13 and week 17 of pregnancy. It is most preferable to collect blood from pregnant females around week 13 in order to enrich for the highest number of fetal cells. Additionally, body fluids other than the peripheral blood may also be used as a source of fetal cells, and they include the amniotic fluid and the lymphatic fluid.

5.2. ENRICHMENT OF FETAL CELLS BY DENSITY GRADIENT CENTRIFUGATION

The present invention relates to methods of rapid and high yield enrichment of fetal cells based on density gradient centrifugation. More specifically, the invention utilizes a precisely determined density of a density gradient solution contained within a specially designed cell-trap centrifugation tube to allow the fetal cells to be collected by decantation in order to maximize cell yield. These steps are taken, because the number of fetal cells in the starting cell mixture is usually very small, so that every effort directed to minimize cell loss during the cell separation process greatly enhances the accuracy of the subsequent use of the isolated cells.

A major advantage of the methods described herein is that a large volume of complete blood may be directly placed on the density gradient. Peripheral blood may be collected in anti-coagulant-containing tubes or by apheresis or leukopheresis. Complete blood does not need to be processed or diluted prior to centrifugation. However, since the methods enrich fetal cells based on their specific buoyant density, it is important that the cells are subject to separation within a relatively short time after their collection from an in vivo source because the density of the cells changes according to their culture or storage conditions. Therefore, in order to obtain optimal enrichment of fetal cells from maternal blood, it is preferred that the blood samples are used within 48 hours after their collection. Most preferably, blood samples should be subjected to density gradient centrifugation within several hours of collection.

The present invention demonstrates that proper adjustments of a gradient material to a specific density, osmolality and pH greatly enhance cell separation. For the enrichment of fetal nucleated red blood cells, a gradient should be adjusted to a density of 1.0720±0.0005 gr/ml, a physiologic osmolality of 270–290 mOsm/kg H2O and physiologic pH 6.8–7.8. In a specific embodiment by way of examples, blood samples of pregnant females are directly loaded into a cell-trap centrifugation tube containing a "PERCOLL" solution (a polyvinylpyrrolidine-coated colloidal silica) filled to a level above the constriction, which has been adjusted to the preferred density of 1.0720±0.0002 gr/ml, osmolality of 280 mOsm/kg $H_2O$ and pH7.4. The density of the "PERCOLL" solution may be adjusted on a densitometer to precisely define its accuracy at least to the fourth decimal place. It should be noted that a variety of other gradient materials may be used to achieve fetal cell enrichment, and they include, but are not limited to, "FICOLL" (a nonionic polymer of sucrose and epichlorohydrin), "FICOLLHYPAQUE" (a mixture of 3,5-diacetamido-2,4,6-triiodobenzoic acid and a nonionic polymer consisting of sucrose and epichlorohydrin), cesium chloride, any protein solution such as albumin or any sugar solution such as sucrose and dextran. However, the density gradient solution should be prepared and adjusted to the appropriate density, osmolality and pH according to that disclosed herein, prior to their use. They should be added to a centrifugation tube in a volume sufficient to allow all the cells having a higher density to pass through during centrifugation. For example, a volume of about 20–25 ml of the solution is generally adequate for separating fetal cells in 20 ml of maternal blood samples.

Any tubes suitable for use in centrifugation may be used for the practice of the invention. In a preferred embodiment, the present invention is directed to a cell-trap tube for the density separation of fetal cells. For the purpose of the present invention, a cell-trap tube refers to a centrifugation tube which contains within it a constriction or a trap and a properly adjusted density gradient material filled to a level above the constriction so that cells having a certain density pass through the opening of the constriction to form a cell pellet in the compartment below the constriction during centrifugation.

Figure 4A:
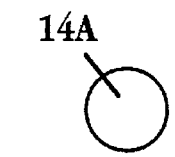
Figure 4B:
Figure 4C:
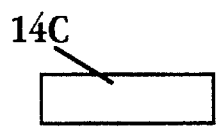
Figure 4D:
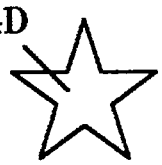
Figure 4E:
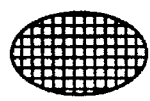

According to a preferred embodiment shown in FIGS. 1A & B, tube 10 includes constriction member 12, which defines central opening 14. The upper surface of constriction member 12 is preferably slightly angled inward, toward opening 14. The bottom surface of the constriction member also may be similarly, slightly angled (although not shown as such in the figures). In an exemplary embodiment, with a tube having an inner diameter of about 2.8 cm, the diameter of opening 14 formed by constriction member 12 is preferably about 0.5 cm. The size of opening 14 is generally not so small as to prevent heavier components of a sample, layered on top of the density gradient solution, from passing through the opening prior to actual centrifugation. Such a movement of components may occur due to normal gravitational forces. In general, the diameter of opening 14 is dictated by the ability to form an increased surface tension across the opening. A restriction that is little more than a rim around the interior of the barrel may be sufficient. Hence, the cross-sectional area of the aperture formed by the constriction member may be as little as about 5% or as great as about 95% of the horizontal cross-sectional surface area of the tube. In addition, the annular member may consist of a mesh or a sieve spanning the horizontal cross-section of the tube. In this case, the annular member is said to comprise a plurality of openings, such as illustrated in FIG. 4E.

Tube 10 is filled with density gradient solution 16 to a level above constriction member 12, or at least above opening 14. Preferably, with reference to a standard 50 ml centrifugation tube, density gradient solution 16 is filled to a level at least about 1 mm above the constriction member. The fluid sample to be separated is layered on the top of the density gradient solution, and the tube and its contents are subjected to centrifugation. Preferably, the sample is carefully layered so that at least about 1 mm of density gradient solution remains between the sample and the top of the constriction member after layering.

Referring to FIG. 1B, following centrifugation, components having densities greater than that of the gradient solution are found in a pellet 20 at the bottom of tube 10. Components having densities less than that of the density gradient solution remain floating at the top of the gradient solution, in an interface 22 between the gradient solution and the remaining portion of the fluid sample solution. The interface portion is then poured off as indicated by arrow 24 in FIG. 1C. The provision of the density gradient solution to a level above the opening as described above helps to prevent the formation of an interface portion below constriction member 12.

Constriction member 12 facilitates pouring off the upper portion by providing a support or nucleus for formation of an intermediate surface tension across the surface of opening 14 when tilted for pouring. This surface tension impedes mixing of upper and lower portions of the tube when the contents of the upper portion are poured out of the tube. Constriction member 12 may be provided as an insert placed into a straight-walled tube. Alternatively, constriction member 12 may be formed as constriction of the tube wall during a molding process in the making of the tube itself. When the constriction member is provided by an insert, the insert may be movable to enable the operator to change the relative volumes of the lower portion 26 and upper portion 28 of tube 10 according to experimental conditions. The position of the constriction member in a molded tube can also be varied, during the manufacturing process, to provide tubes of differing relative upper and lower portion volumes. For example, in the isolation of cells from peripheral blood, a 20 ml sample of blood requires lower portion 26 to be about 15 ml in order to accommodate the relatively large amount of red blood cells that migrate to the pellet during centrifugation. By comparison, a 20 ml sample of apheresis or buffy-coat blood would require only about 10 ml in the lower portion.

In many applications, it will be desirable to collect only the supernatant fraction containing the interface portion. In such cases, the pellet is discarded with the tube. In other cases, the pellet can be removed by mechanical manipulation/disruption. For example, the tube can be inverted and subjected to vortex mixing. Such mixing will disrupt the pellet into the adjacent liquid phase and will induce movement of this liquid phase and disrupted cells from the lower or collection portion of the tube into the upper portion of the tube.

An advantage of the present invention is that the low density material above the constriction member is separated from material beneath by the simple act of pouring. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials. In addition, unlike conventional straight-wall tubes, if the centrifuge tube of present invention is dropped or accidentally inverted, the contents will not readily mix due to the presence of the constriction member. Moreover, once separation has taken place, the solution presesolution present above the constriction member can be mixed in the tube, without disturbing (or fear of contamination by) the contents of the tube below the constriction member.

In an alternative preferred embodiment, tube 10 may be provided with insert or shield 30, as shown in FIGS. 2A and 2B. Shield 30 is provided above constriction member 12 to facilitate layering of the sample onto the gradient solution. Shield 30 may take the form of a roughly concentric insert placed in the upper portion of the tube and extending at least partially around the tube. In use, the operator pipettes material between shield 30 and the tube wall. The shield directs the material along the side of the tube to the top of the density gradient solution, while minimizing disturbance of the solution. As shown in FIG. 2B, tube 10 is a clear plastic or glass, with constriction member 12 formed as a separate insert. Shield 30 can be held in the upper portion of the tube, for example, by interference fit with spacers 31 biasing against the tube wall. Alternatively, shield 30 could be formed as a part of the tube.

The separation of materials may be further enhanced by the addition of valve 40 to the constriction member, as shown in FIG. 3. The valve 40 is located across opening 14. Valve 40 may be a one-way valve, or a valve that only opens upon application of a threshold centrifugal force. The valve can be formed by providing flaps of a softer material over the opening. In a preferred embodiment, the force required to open valve 40 would be about 850 times the normal force of gravity. Valve 40 thus allows heavy cells to pass through during initial centrifugation, and then keeps those cells in place, allowing for further processing of the lighter cells of interest located above the valve (such as washing or mixing of the cells). In this way complete and final manipulation of the cells can be performed in a single sterile container.

The shape of opening 14 is not limited to a circular shape, though in general, a funnel-shaped restriction forming a roughly circular shape 14A will be preferred. As shown in FIGS. 4A–D, the opening may also be oval 14B, rectangular 14C, star-shaped 14D, or any other shape that would create a restriction.

Figure 5A:
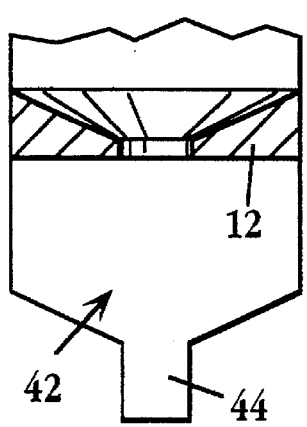
Figure 5B:
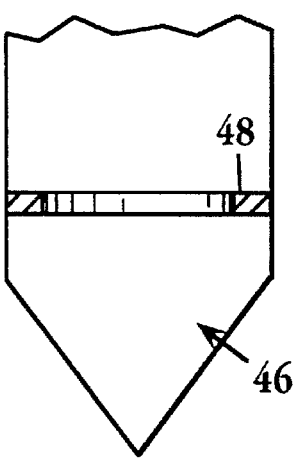
Figure 5C:
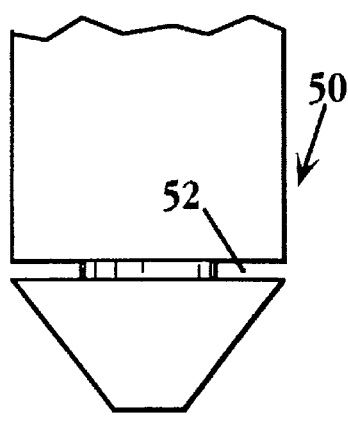
Figure 5D:
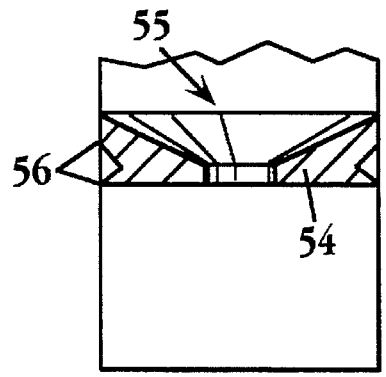
Figure 5E:
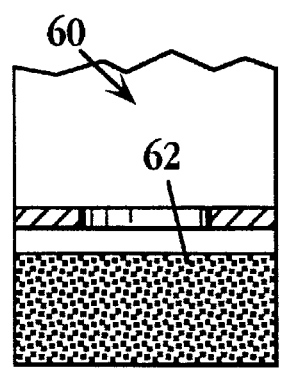
Figure 5F:
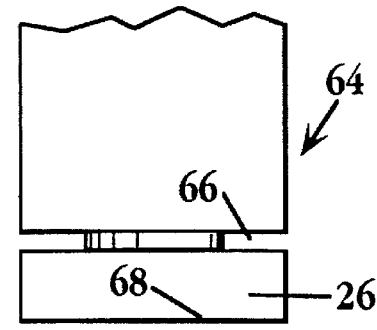

FIGS. 5A–F are illustrations of alternative shapes and designs for the tube and constriction member according to the invention. FIG. 5A shows alternative tube 42 having a separate bottom compartment 44 for receiving the pellet to provide optimal collection of cells. Constriction member 12 is as previously described; it is funnel shaped on its upper surface and formed from a separate insert of plastic or, preferably, silicone. FIG. 5B shows a tube 46 with a pointed bottom wall. Tube 46 with the pointed bottom wall also enhances cell collection by allowing the heavier cells to form a better pellet, which may be desired if the cells are to be collected. Constriction member 48 is again an insert, but with a flat upper surface and wider opening. FIG. 5C illustrates alternative tube 50 with an integrally molded constriction member 52. FIG. 5D shows an alternative constriction member 54 that facilitate movement within tube 55 to adjust the relative volumes of the upper and lower portions. For this reason constriction member 54 has annular extendings contact points 56. The constriction member will only contact the tube at these points, which create a fluid tight seal, but allow for easier adjustability. Tube 55 also has a flat bottom. FIG. 5E illustrates a further alternative embodiment of the present invention, wherein tube 60 includes cell trapping material 62, such as a sponge or gel. Material 62 may contain compounds that specifically bind certain cell types or toxins that kill specific cell types. Material 62 also may be made of a magnetic material if desired. Tube 64, shown in FIG. 5F, illustrates a further example of an integrally formed constriction member 66 in a tube with a flat bottom wall 68. Construction member 66 is located such that lower portion 26 has a smaller relative volume.

FIGS. 6A and B illustrate further alternative embodiments of the tube according to the invention. In each, two constriction members are provided. Second constriction member 12A is located above first constriction member 12B to create more compartments to allow separation of cells of differing densities. In FIG. 6A, the constriction members are shown as separate inserts, whereas they are integrally formed with the tube in FIG. 6B. Additional constriction members could also be added if a sample of several different densities is to be separated.

It will be applied by persons of ordinary skill in the art that the embodiments of FIGS. 2–6 are illustrated herein without density gradient solution for the sake of clarity only. Preferably, each embodiment would contain density gradient solution as described herein in connection with the embodiment of FIG. 1A.

5.3. DENSITY ADJUSTED CELL SORTING

Figure 7A:
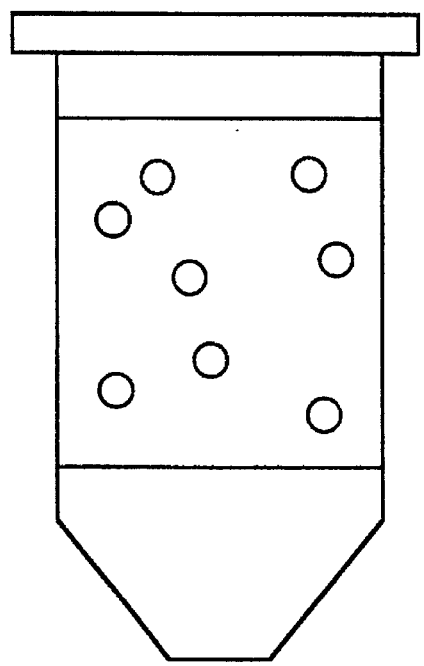
Figure 7B:
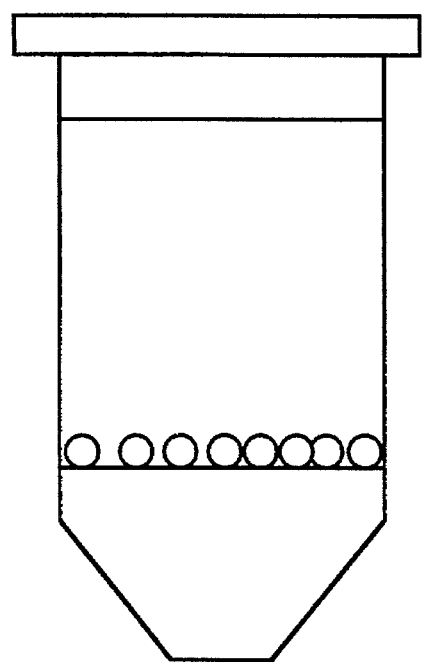
Figure 7C:
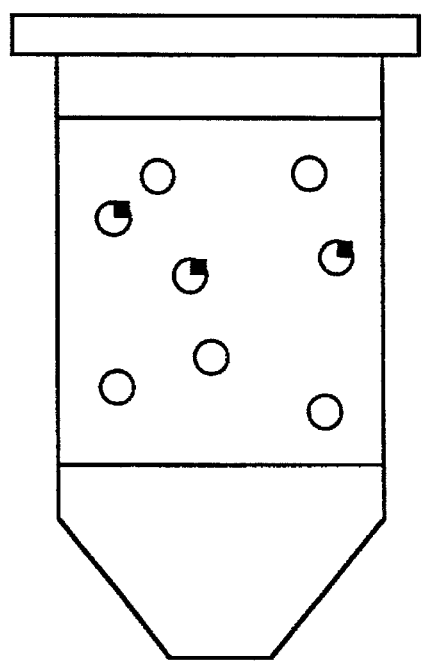
Figure 7D:
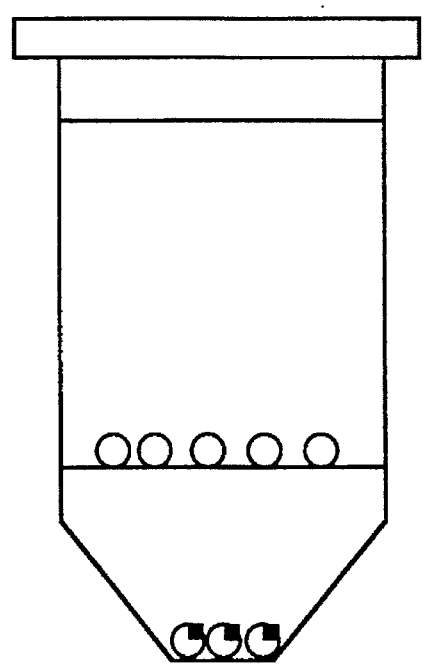

Density gradient centrifugation is a method of separating cells based on the different densities of cell types in a mixture. The method is often used in a single step to separate cells into two compartments which contain cells that are either lighter or heavier than a specific density of the gradient material used. However, due to the imprecision of the procedure, the use of a single density may not allow the cells of interest to be enriched to a significant level of purity, especially if the cells are present in a low number among many undesired cell populations. Thus, density gradient centrifugation is most often carried out through repetitive steps based on a series of different density gradients or in combination with affinity chromatography, cell panning, cell sorting, and the like. Alternatively, discontinuous density gradient centrifugation may be performed using multiple layers of the different gradient densities. This method allows cells of different densities to form zones or bands at their corresponding densities after centrifugation. The cells in the different zones are then collected by suction through a pipette placed at the appropriate location. Such a method is difficult to carry out in a routine manner in a clinical setting because it requires skilled personnel for the preparation of the gradient, and there is often mixing between the different layers of the density solution before and/or after centrifugation that potentially disrupts cell separation. Most importantly, the above-described procedures require multiple steps that unavoidably cause substantial cell loss, thus they are not amenable for the separation of cells present in a low number within a mixture in a routine manner. The present invention circumvents these problems by combining density gradient centrifugation and affinity cell separation into a single method referred to as density adjusted cell sorting. This method is preferably performed in a cell-trap tube. This method modifies the conventional positive and negative selection by solid phase binding methods, and combines it with the specific density of 1.0720±0.0005 gr/ml, preferably ±0.0002 gr/ml, at an osmolality of 80±10 mOsm/kg $H_2O$ for fetal cell separation. FIG. 7A–D demonstrates the use of density adjusted cell sorting as (FIGS. 7C and 7D compared to conventional density gradient centrifugation (FIGS. 7A and 7B) While the conventional methods are able to concentrate many irrelevant cell types to form a pellet, there are still a large number of undesired cell types trapped at the interface with the cells of interest. However, density adjusted cell sorting provides for the use of cell type-specific binding agents conjugated to heavy carrier particles with specificity for antigens expressed by the undesired cell populations, and incubating such agents with the cell mixture prior to centrifugation, so that such density-adjusted cells (solid squares and open circles, FIGS. 7C and 7D) would be pelleted during centrifugation. Thus, although these cells are normally lighter than the gradients, density, a heavier S density is imparted to them due to the higher density of the carrier particles which are rendered cell type-specific by the antibodies used. When density adjusted cell sorting is applied to a cell mixture which is overlaid onto a customized density gradient contained within a cell-trap centrifugation tube, a single centrifugation step allows for substantial enrichment of a cell type of interest from any cell mixture. Example 6, infra, shows that complete blood from pregnant females could be directly incubated with carrier particle-coated-anti-CD45 antibodies which react with most leukocytes. Since fetal nucleated red blood cells do not react with anti-CD45 to any significant degree, the vast majority of the non-red blood cells are rendered heavier than the density material and pellet during centrifugation. A variety of such cell type-specific binding agents may be used to target specific cell types in the blood. These agents encompass antibodies such as anti-CD3, anti-CD4, anti-CD5 and anti-CD8 specific for T cells; anti-CD12, anti-CD19 and anti-CD20 specific for B cells; anti-CD14 specific for monocytes; anti-CD16 and anti-CD56 specific for natural killer cells; and anti-CD41 for platelets. Many of these antibodies are commercially available in a form already conjugated to various types of particles (AMAC, DYNAL). In addition, cell type-specific binding agents include lectins such as wheat germ agglutinin and soy bean agglutinin, growth factors and cytokines. Alternatively, a positive selection procedure may be used to cause the nucleated red blood cells to be heavier than their normal density so that they are pelleted during centrifugation. In this case, mature red blood cells may be removed and then antibodies directed to glycophorin A or CD71 coated on carrier particles are used to pellet all remaining nucleated red blood cells. Furthermore, antibodies directed to any cell surface marker may be directly linked to heavy particles for use in density adjusted cell sorting, following conjugation methods well known in the art. It is noteworthy that when density adjusted cell sorting is applied, the specific density of the gradient is less critical, as long as the undesired cells are all rendered heavier. Although the methods of the present invention do not provide for the isolation of fetal cells to absolute purity, they allow the cells to be enriched substantially so as to enhance their use in subsequent prenatal diagnosis. A number of commercially available carrier particles may be used in the present invention and include, for example, organic polymers, e.g. polyethylene; polypropylene; polyvinyl compounds e.g. polyvinylchloride, polyacrylonitrile, polyacrylate, polymethacrylate, polycarbonate and copolymers thereof; polystyrene latex; nylon; polyterephthlate; and the like, or inorganic polymers, e.g. glass or silica particles; cellulose, polysaccharides, e.g. agarose, cellulose, dextran Sepharose, Sephadex, etc., or combinations thereof. The carrier particles may be from naturally occurring polymers, modified naturally occurring polymers and synthetic addition and condensation polymers. A preferred carrier particle of the present invention is a silica particle between 0.1–5.0 microns coupled to an aminopropyl group and having a density of greater than 1.08 gr/ml. U.S. Pat. Nos. 4,927,750 and 4,927,749, issued May 22, 1990, describe examples of modified silanes which may be used in the present invention as carrier particles. Various carrier particles are commercially available from, for example, Bangs Laboratories, Inc., Carmel, Ind.; Pharmacia Fine Chemicals, Piscataway, N.J.; Sigma Chemical Company, St. Louis, MO; Bio-Rad, Richmond Va. A; AMAC, Inc.; etc. A preferred heavy carrier particle of the present invention is one having a density greater than 1.08 gr/ml and a particle size of 0.1 micron to 5.0 micron such that the carrier particles will be pelleted upon centrifugation, as well as one having the capability of binding, either directly or indirectly to cell-type specific binding agents.

Immobilization of a cell-type specific binding agent to carrier particles can be achieved by a variety of techniques known to those skilled in the art. Such techniques are described in, for example Bangs (*The Latex Course* (1992), available from Bangs Laboratories, Inc. Carmel, Ind.) Yoshioka et al. (*Journal of Chromatography* 566:361–368 (1991); Pope et al. (*Bioconjuate Chem.* (1993) 4:166–171); Harlow and Lane 1988 (*Antibodies: A Laboratory Manual*, Colorado Spring Harbor Laboratory); *Avidin-Biotin Chemistry: A Handbook*, 1992, ed. Savage et al., pub. PIERCE; Hermanson et al., *Immobilized Affinity Ligand Techniques*, 1992, pub. Academic Press, Inc. Binding techniques include, for example, simple physical absorption or adsorption where the cell-type specific binding agent is bound directly to the carrier protein without the use of functional groups; complex adsorption where a second binding agent, e.g. BSA, is co-adsorbed to the carrier particle and forms the basis for binding functional groups; and covalent bonding of the binding agent to the carrier particle. The biotin-strepavidin affinity system may also be used in the present invention to bind cell-type specific binding agents to the carrier particles. Various particle surface chemical reactions for covalent coupling are known to those of skill in the art and include, but not limited to, carboxylic acid, primary or aliphatic amine, aromatic amine or aniline, chloromethyl (vinyl benzyl chloride), amide, aldehyde, hydroxyl, thio, hydrazide, epoxy, sulfate and sulfonate. Other coupling chemical reactions are described in Bangs, Uniform Latex Particles (1984).

In the present invention, it is preferred that the direct or indirect binding of the cell-type specific binding agent to the carrier particle be performed in excess binding agent to allow for maximum coverage of the surface of the carrier particle, thereby reducing the potential for non-specific binding. Carrier particles may also be subjected to blocking agents, e.g. casein, gelatin and Tween to fill any unoccupied sites on the carrier particle in order to reduce non-specific binding.

In one illustrative example of a coupling reaction, carboxyl groups on the carrier particle surface can be made reactive with the available amino groups on the cell-type specific binding agent. Other means of binding cell-type specific binding agent to particle surfaces include employing activated carboxylic acids, carbodiimides, i.e., (1-ethyl-3-(3-dimethylaminopropyl)carbodiimide or EDAC, imido esters, active alkyl halides, etc., to form amido, amidine or amino linkages.

A preferred carrier particle of the present invention is an aminopropyl silica particle wherein the amino groups have been coupled to the silica particle through a glutaraldehyde linkage.

5.4. USES OF FETAL CELLS ISOLATED FROM MATERNAL BODY FLUIDS

The fetal cells enriched by the methods described herein may be used for a variety of genetic testing procedures. For example, the cells may be collected according to the methods described above, then cultured and used for the preparation of metaphase in cytogenetic analysis. This technique may be used for detecting chromosomal abnormalities and gender determination. When the cells are to be cultured, the separation procedure must be performed under sterile conditions.

In addition, the fetal cells may be reacted with molecular probes for more sensitive detection of genetic anomalies using PCR and FISH. These methods are useful for prenatal diagnosis of chromosomal abnormalities such as trisomy 18, trisomy 21, Turner syndrome, trisomy 13, Penta X Syndrome, XYY syndrome, Klinefelter syndrome, to name a few. Furthermore, molecular probes may be designed for the diagnosis of cystic fibrosis, muscular dystrophy, fabry disease, Gaucher disease, hemoglobinopathies, hemophilia, phenylketonuria, etc.

6. EXAMPLE

ENRICHMENT OF FETAL NUCLEATED RED BLOOD CELLS FROM MATERNAL BLOOD

6.1. MATERIALS AND METHODS

6.1.1. PREPARATION OF DENSITY GRADIENTS

"PERCOLU" solution was purchased from Pharmacia Biotech (Uppsala, Sweden) and stored at 4° C. according to the recommendation of the vendor. A stock solution was prepared by mixing 12 parts of "PERCOLL" with 1 part of 10× calcium and magnesium-free phosphate buffered saline (PBS). The pH of the solution was adjusted to 7.4 and the osmolality to 280±10 mOsm/Kg $H_2O$. For use in separating fetal nucleated red blood cells in a blood sample, the stock solution was further diluted with calcium and magnesium-free PBS to a density of 1.0720±0.0005 gr/ml and used at room temperature. It was important to adjust the density of the gradient to an accuracy within ±0.0005 gr/ml, preferably within 0.0002 gr/ml of 1.0720 gr/ml in order to ensure reproducibility and accuracy of cell separation. This was done by a high precision digital density meter such as DMA 48 (Anton PAAR U.S.A., Ashland, Va.). All procedures were performed under sterile conditions and at room temperature.

6.1.2. COLLECTION AND PROCESSING OF BLOOD SAMPLES

Peripheral blood was collected from pregnant females in anti-coagulant-containing tubes. The collection was performed before week 20 of pregnancy because the number of fetal cells circulating in maternal blood generally began to decline after week 17 of pregnancy. In fact, the preferred end point for blood collection was before week 17 of pregnancy with week 13 being the optimal time point for highest numbers of fetal cells in maternal circulation. After collection, the blood samples were processed within 48 hours, since there was a prominent reduction in accuracy of cell separation on the density material with samples used 48 hours after collection.

6.1.3. DENSITY GRADIENT CENTRIFUGATION OF PERIPHERAL BLOOD

Complete blood samples were layered on a "PERCOLL" gradient previously adjusted to a density of 1.0720±0.0002 gr/ml, an osmolality of 280 mOsm/Kg $H_2O$, and a pH of 7.4 in a 50 ml conical cell-trap tube. The tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the region below the constriction were prevented from pouring off when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the upper region, a cell-trap could also be used to facilitate this step. In this alternative embodiment, a modified 50 ml cell-trap tube was used in which the constriction was placed near the bottom of the tube so that a small volume of about 0.5 ml was below it. This design would protect the pellet and reduce cell loss during removal of the fluid above the pellet after centrifugation. This specific feature would also allow the method of the invention to be used in an automated fashion without the need for a subsequent cell sorting step, which was performed to reduce contaminating cells, particularly platelets.

In order to compare the cell separation method described in the preceding paragraph with conventional methods, the following procedure was also carried out as a control. This procedure was similar to previously published methods known in the art (Bianchi et al., 1990, Proc. Natl. Acad. Sci. USA 87:3279). The blood sample was collected as described above and diluted 1:4 in PBS. The diluted blood was layered on "FICOLL-HYPAQUE" (Pharmacia) in 4 different 15 ml tubes. The density of the stock "FICOLU" solution was at 1.077±0.001 gr/ml and the osmolality at 320 mOsm/kg $H_2O$ as published by Pharmacia. The tubes were centrifuged at 850×g for 20 minutes at room temperature. The cells at the interface above the "FICOLL" were collected with a pipette and transferred to two 15 ml tubes. The tubes were filled to the top with PBS and spun at 650×g for 10 minutes at room temperature. The fluid on top of the pellet was aspirated with a pipette, and the pellet resuspended in PBS. In addition, experiments were also performed using cell-trap tubes with "FICOLL" solution in an effort to increase cell yield.

6.1.4. AFFINITY SEPARATION BY A MAGNETIC FIELD

The fetal nucleated red blood cells resuspended in PBS after density gradient centrifugation described in Section 6.1.3 were further enriched through removal of CD45+ leukocytes by incubating the cells with an anti-CD45 monoclonal antibody (clone ALB-12) (Biodesign International, Kennebunk, Me.) for 30 minutes at 4° C. The unbound antibodies were removed by washing the cells in PBS. A goat-anti-mouse antibody conjugated to magnetic particles (Immunocon) was added to the cells for 30 minutes at 4° C. The cells were washed in PBS and exposed to a magnetic field which attracted the magnetic particle-coated CD45+ leukocytes, while the fetal nucleated erythroid and trophoblast cells remained in solution. The fetal cells were collected with a pipette and washed once in PBS. The cells were then tested by antibody staining and flow cytometric analysis to determine the number of nucleated red blood cells.

6.1.5. DENSITY ADJUSTED CELL SORTING

Complete blood collected from pregnant females was incubated with 1.4µ aminopropyl glass beads (Bangs Laboratories Inc., Carmel, Ind.) that were glutaraldehyde coated with an anti-CD45 antibody (ALB-12) for 45 minutes at room temperature. The entire blood cell mixture was layered on "PERCOLL" (1.0720±0.0002 gr/ml, 280 mOsm/Kg $H_2O$, pH 7.4) in a 50 ml cell-trap tube. The tube contained about 15 ml of "PERCOLL" below the constriction and about 5 ml above it. It was critical to completely fill the volume under the constriction with "PERCOLL" to prevent the formation of air bubbles. The tube was centrifuged at 850×g for 30 minutes at room temperature. The leukocyte-depleted cell population was collected from the interface above the "PERCOLL" by pouring off the entire upper region of the tube into a 50 ml tube. The cells were spun at 650×g for 10 minutes at room temperature, and the fluid on top of the pellet removed with a pipette. The cells in the pellet were resuspended in PBS. Alternatively, the second centrifugation step could be carried out in a modified cell-trap tube as described in Section 6.1.3, supra. Additionally, a second density adjusted cell sorting could also be performed using antibodies such as anti-CD41 to specifically remove platelets.

6.1.6. ANTIBODY STAINING AND FLOW CYTOMETRIC ANALYSIS

The leukocyte-depleted cell population in PBS were treated with the DNA dye LDS 751 (Exciton, Inc., Dayton, Ohio) and erythroid lineage specific FITC-conjugated monoclonal antibodies such as anti-glycophorin A and anti-CD71 (Becton Dickinson, Inc., San Jose, Calif.). The LDS 751 dye distinguished between nucleated and a nucleated cell. One million cells were incubated with 10 µl antibodies for 30 minutes at 4° C. in the presence of 5% rabbit serum and LDS 751. The cells were washed twice with PBS and fixed in 1% paraformaldehyde. The antibody-bound cells were analyzed by flow cytometry for which statistical analysis was performed on $10^4$ flow events using a FACSScan system equipped with a LYSYS II program.

6.2. EXAMPLES

6.2.1. HIGH YIELD OF NUCLEATED RED BLOOD CELLS FROM MATERNAL BLOOD

The cell separation methods of the present invention provided a rapid procedure for the high yield enrichment of fetal cells in a cell mixture in maternal blood. Fetal nucleated red blood cells were chosen for enrichment because they represented the more abundant population of fetal cells in maternal blood that could be readily used for genetic testing by applying a number of well-established techniques. However, the number of fetal nucleated red blood cells in maternal blood were still an extremely minor population as compared to other adult nucleated cells. Thus, a rapid enrichment method was designed to minimize cell loss and maximize the number of fetal cells available for subsequent testing.

Table 1 presents results from an experiment in which "PERCOLL" was used as the density gradient material. "PERCOLL" was prepared and adjusted to physiologic osmolality of 280 mOsm/kg $H_2O$ and physiologic pH of 7.4. However, when the gradient was adjusted to different densities, the results showed that while a density of 1.0720 gr/ml or above produced at least about 50% recovery of nucleated cells from the total nucleated cell population prior to centrifugation, there was a substantial contamination of the interface with mature red blood cells when the gradient was adjusted to a density of 1.0750 gr/ml or above. Thus, in order to recover a high percentage of total nucleated cells from the starting cell mixture, but reduce mature red blood cell contamination which was undesirable for further processing of the sample, the density of 1.0720 gr/ml was chosen and further defined to an accuracy of within ±0.0002 gr/ml. These results demonstrate that there is a narrow range of densities which may be used for the high yield enrichment of nucleated cells from a blood sample.

When four cell separation methods were compared for nucleated red blood cell yield, the two methods of the present invention produced substantially higher percentages of nucleated red blood cells than the conventional method. Table 2 shows that the cell-trap tubes containing "PERCOLL" at a density of 1.0720±0.0002 gr/ml produced about a 20 fold higher number of nucleated red blood cells than the conventional method using stock "FICOLL" at a density of 1.077±0.001 gr/ml and 320 mOsm/kg $H_2O$. FIGS. 8A–8C are a visual comparison of the nucleated cells enriched by three methods. "Percoil" plus cell-trap is superior than the other two methods in cell yield. FIG. 9A–9C shows three nucleated red blood cells at different stages of differentiation isolated by the "PERCOLL" plus cell-trap procedure. Therefore, this result statistically increased the total number of fetal nucleated red blood cells for subsequent genetic testing. In fact, the specific procedure also enriched for fetal trophoblast cells. Furthermore, the method involving density adjusted cell sorting produced comparable results as the method requiring magnetic field depletion of CD45+ undesired cell populations. However, it should be noted that if the stock "FICOLL" was adjusted to the appropriate density and osmolality, it could be used to obtain comparable cell yield as that achieved by the "PERCOLL" used herein.

TABLE 1

| Density of "PERCOLL" (gr/ml) | Percentage of Nucleated Cells Recovered from Interface After Centrifugation | Percentage of Mature Red Blood Cell Contamination |
| --- | --- | --- |
| 1.0820 | 60% | 21% |
| 1.0790 | 58% | 21% |
| 1.0770 | 56% | 25% |
| 1.0750 | 45% | 20% |
| 1.0720 | 50% | 2% |
| 1.0700 | 21% | 2.2% |
| 1.0640 | 25% | 2.1% |
| 1.0610 | 23% | 1.7% |

TABLE 2

| | Cell Number Before Separation | Percentage of Nucleated Cells Recovered from Interface | | Percentage of Nucleated Red Blood Cells | Percentage of Nucleated Fetal Red Blood Cells |
| --- | --- | --- | --- | --- | --- |
| | | After Density Centrifugation | After Anti-CD45 Depletion | | |
| Conventional Method Using "FICOLL" | $10^7$ | 14% | 0.2% | 0.01% | Undetectable |
| "FICOLL" plus Cell-trap | $10^7$ | 16% | 0.17% | 0.01% | 0.05% |
| "PERCOLL" Plus Cell-trap | $10^7$ | 54% | 1.7% | 0.21% | 0.41% |
| "PERCOLL" Plus Cell-trap Plus Density Adjusted Cell Sorting | $10^7$ | 3.3% | Not Applicable | 0.23% | Not Done |

Thus, the cell-trap tubes containing a specific density gradient material coupled with density adjusted cell sorting provide for a rapid procedure which combines two steps into a single step to process a large volume of blood samples for high yield enrichment of nucleated red blood cells. This method is also more cost-effective because it does not require the use of a magnetic field, and require fewer working hours to process multiple samples.

6.2.2. HIGH YIELD OF FETAL CELLS FOR GENETIC TESTING

The nucleated red blood cells enriched by the methods described in Section 6.2.1, supra, were subsequently examined for the presence of fetal cells. The enriched cell preparations obtained from donors who were known to be carrying a male fetus were selected for use in FISH analysis. The cells were incubated with an X-chromosome-specific probe linked to a green fluorescence dye and a Y-chromosome-specific probe linked to a red fluorescence dye. Therefore, fetal nucleated red blood cells were identified as cells with nuclei that contained a red spot and a green spot under a fluorescence microscope, while other cells were of maternal origin. The far right column of Table 2 shows that there was an eight fold increase in the number of XY (fetal) chromosomes in the cell populations prepared by one method of the invention over that by the conventional method. However, it is of interest to note that the method of using cell-trap and "FICOLU" also increased the number of fetal nucleated red blood cells to the detection threshold over the same gradient practiced without cell-trap tubes, indicating that the celltrap was useful in increasing cell yield. It is also noteworthy that in order to obtain reliable diagnostic results involving techniques such as FISH, it is generally necessary to enrich the fetal cells to at least 0.1% of the final cell preparation in order for the enrichment method to be used as a routine procedure. In other words, a reliable diagnosis by FISH needs to examine at least 10,000 total cells in which there are at least 10 fetal cells. One method of the invention is shown herein to have clearly exceeded this limit to have enriched fetal cells to a level of 41 cells/10,000 total cells analyzed.

7: EXAMPLE: METHOD FOR BINDING ANTIBODY TO GLASS BEADS

7.1 PREPARATION OF THE BEADS

Silica beads (1.4 microns) obtained from Bangs Laboratories, Carmel, Ind. were washed with concentrated HCl for 2 hours at room temperature and vortexed intensely every 15 minutes to brake up bead clumps. After washing, the beads were centrifuged at 850 g for 5 minutes. The HCL containing supernatant was decanted and the beads were washed with deionized $H_2O$ with intensive vortexing to brake up the clumps.

The beads were incubated at room temperature overnight in concentrated nitric acid with constant stirring using a magnetic stirrer. The beads were then centrifuged at 850 g for 5 minutes and washed 3 times with deionized water, using 50, ml of deionized $H_2O$ at each step. The beads were vortexed intensely in between each wash to avoid bead clumping. To prevent microbacterial contamination, the beads were stored at 0–4 degrees centigrade in deionized $H_2O$ until further Use.

7.2 SILANIZATION OF THE BEADS

To silanize the beads, either 3-aminopropyltriethoxysilane, (3-iodopropyl)

trimethoxysilane or [1–9trimethoxysilyl)-2(m-(or p) chloromethyl)phenyl]ethane were used. Forty mls of silane solution (a 10% solution in 95% ethanol/deionized H$_2$O) was added per 4 gr of beads. The bead mixture was rotated end over end for 1 hour at room temperature. The beads were centrifuged at 850 g for 5 minutes and the excess silane was washed off using 95% ethanol/deionized H$_2$O in a volume of 100 ml. The beads were vortexed intensely in between each wash step to avoid bead clumping. After the washing step, the beads can be dried and stored. Alternatively the beads can be stored in 95% ethanol/deionized H$_2$O in the cold which prevents clumping of the beads.

7.3 ANTIBODY COUPLING TO THE AMINOPROPYL GLASS

The silanized beads were incubated overnight in 2.5% glutaraldehyde at room temperature. The next day, the beads were centrifuged at 850 g for 5 minutes and the free glutaraldehyde was washed off with deionized H$_2$O in a volume of 100 ml per 5 gr beads. The beads were vortexed intensely in between each wash step to avoid bead clumping.

The antibody was added to the aminopropyl beads in an excess, at least 3 mg/m$^2$ total bead surface and rotated end over end overnight at room temperature. The next day, the beads were centrifuged at 850 g for 5 minutes and the free protein was washed off with 100 ml of deionized H$_2$O. The beads were vortexed intensely in between each wash step to avoid bead clumping. The beads were stored in deionized H$_2$O containing 0.1 sodium azide in the cold. The final bead suspension should contain 70–90% single beads and 10–30% predominantly duplet and triplet beads.

The binding efficiency of the antibody conjugated beads (in terms of the percent of beads that are coated) can be determined using flow cytometric analysis and a fluorescinated antibody directed to the coupled antibody. Alternatively, the antibody may be added to the silanized beads directly without the glutaraldehyde linking.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of enriching fetal cells from a cell mixture, comprising:
    layering a cell mixture containing fetal cells onto a density gradient solution contained in a centrifuge tube, said tube having a first closed end defining an inner bottom wall and an opposite open end, an annular member disposed in said tube and defining an opening therethrough, wherein said opening has an area less than the area of a cross section of said tube, said annular member defining a lower portion of the tube extending between said member and said tube bottom wall and an upper portion above said annular member, said tube containing a density gradient solution which fills said lower portion and a part of said upper portion to a level above said annular member prior to centrifugation of said tube,
    said density gradient solution having an osmolality of 280±10 mOsm/kg H$_2$O and a specific density within 0.0005 gr/ml of the specific density of said fetal cells;
    centrifuging said tube at a gravitational force sufficient to pellet cells having specific densities greater than the specific density of the density gradient material in said tube; and
    collecting from the upper portion of said tube an enriched population of fetal cells.

2. The method of claim 1 wherein the specific density of the density gradient material is within 0.0002 gr/ml of the specific density of said fetal cells.

3. The method of claim 2 wherein the specific density of the density gradient material is 1.0720 gr/ml.

4. The method of claim 3 wherein the fetal cells are nucleated red blood cells.

5. The method of claim 3 wherein the fetal cells are trophoblasts.

6. The method of claim 1 wherein the fetal cells in the upper portion are collected by decantation.

7. The method of claim 1 further comprising incubating said cell mixture with a cell type-specific binding agent linked to carrier particles prior to centrifugation, said particles having a specific density that is at least 0.001 gr/ml greater than the specific density of said density gradient solution.

8. The method of claim 7 wherein the cell-type specific binding agent specifically binds to non-fetal cells.

9. The method of claim 8 wherein the agent is an antibody.

10. The method of claim 9 wherein the antibody is directed to CD45 antigen.

11. The method of claim 7 wherein the particles are glass beads.

12. The method of claim 11 wherein the beads are silane activated.

13. The method of claim 12 wherein the silane is 3-aminopropyltriethoxy silane.

14. The method of claim 1 wherein the density gradient solution is selected from the group consisting of "PERCOLL", "FICOLL", "FICOLL-HYPAQUE", albumin, sucrose and dextran.

15. A centrifugation tube, comprising:
    a tube adapted for centrifugation having a first closed end defining an inner bottom wall and an opposite open end;
    an annular member disposed in said tube and defining an opening therethrough, wherein said opening has an area less than the area of a cross section of said tube, said annular member defining a lower portion of the tube extending between said member and the tube bottom wall and an upper portion above said annular member; and
    a density gradient solution having a density of 1.0720±0.0002 gr/ml, and filling said lower portion and a part of said upper portion of said tube to a level above said annular member.

16. The tube of claim 15, wherein said density gradient solution fills the upper portion to a level at least about 1 mm above said annular member.

17. The tube of claim 15, wherein said annular member is formed integrally with said tube.

18. The tube of claim 15, wherein said annular member is slideably disposed within said tube to permit adjustment of the volume of the lower portion.

19. The tube of claim 15 wherein said annular member defines a plurality of openings.

* * * * *